United States Patent [19]
Palmiter et al.

[11] Patent Number: 4,579,821
[45] Date of Patent: Apr. 1, 1986

[54] CONTROL OF DNA SEQUENCE TRANSCRIPTION

[75] Inventors: Richard D. Palmiter, Seattle, Wash.; Ralph L. Brinster, Gladwyne, Pa.

[73] Assignee: University Patents, Inc., Westport, Conn.

[21] Appl. No.: 324,111

[22] Filed: Nov. 23, 1981

[51] Int. Cl.[4] .................. C12N 15/00; C12N 5/00; C12N 1/00; C12P 21/00

[52] U.S. Cl. ................. 435/172.3; 435/68; 435/194; 435/240; 435/317; 935/6; 935/34; 935/36; 935/53; 935/70; 935/111

[58] Field of Search ............. 435/172, 240, 241, 317, 435/172.3; 536/27; 936/43, 56, 27, 34, 36; 935/6, 34, 36

[56] References Cited

PUBLICATIONS

Durnam et al., Isolation and Characterization of the Mouse Metallothionein-I Gene, *Proc. Natl. Acad. Sci.* vol. 77, 80, pp. 6511–6515.
Wagner et al., The Human Beta Globin Gene and a Functional Viral Thymidine Kinase Gene in Developing Mice, *Proc. Natl. Acad. Sci.* v78.
Watson, *Molecular Biology of the Gene*, 1977, 3rd Ed. 1981, pp. 5016–5020.
Benjamin, Inc., London, pp. 561–562.
Karin, Regulation of Metallothionein Synthesis in HELA Cells, *Diss. Abstr. Int.*, B 1980, v40(9) 4084 (date of Diss, 1979).

*Primary Examiner*—Alvin E. Tanenholtz
*Attorney, Agent, or Firm*—Marshall, O'Toole, Gerstein, Murray & Bicknell

[57] ABSTRACT

The transcription of DNA sequences in living cells is subjected to external regulation by incorporation of promoter/regulator DNA sequences responsive to metals and/or steroids. More particularly, regulation of the transcription of selected exogenous DNA sequences incorporated into eukaryotic host cells is facilitated by operative association (e.g., fusion) of the selected sequence to a promoter/regulator DNA sequence which is positively or negatively responsive to environmental variation in the concentration of heavy metal ions and/or steroid hormones. As an example, a structural gene for thymidine kinase from herpes simplex virus, fused to the promoter/regulator DNA sequence of a mouse metallothionein-I gene and incorporated on a suitable DNA plasmid vector, is introduced into mouse embryos and stably incorporated therein. Gene expression in differentiated cells of adult mice resulting from the embryos is subsequently regulatable by administration of heavy metals such as cadmium or steroid hormones such as the glucocorticoid, dexamethasone.

4 Claims, 1 Drawing Figure

CONTROL OF DNA SEQUENCE TRANSCRIPTION

BACKGROUND

The present invention relates generally to manipulation of genetic materials and, more particularly, to methods and materials useful in subjecting the transcription of particular DNA sequences to selective regulation by external control.

"Genetic materials" may be broadly defined as those substances which program for and guide the manufacture of cellular (and viral) constituents and the responses of cells and viral particles to environmental changes. The genetic material of all living cells and viruses (except the so-called "RNA viruses") comprises a long chain, polymeric substance known as deoxyribonucleic acid ("DNA"). The repeating units of the DNA polymer are known as nucleotides. Each nucleotide consists of one of four nucleic acids (adenine, guanine, cytosine and thymine) bound to a sugar (deoxyribose) which has a phosphate group attached. Ribonucleic acid ("RNA") is a polymeric nucleotide comprising the nucleic acids, adenine, guanine, cytosine and uricil, bound to a ribose molecule having an attached phosphate group.

Most simply put, the programming function of genetic materials is generally effected through a process whereby DNA nucleotide sequences (genes) are "transcribed" into relatively unstable messenger RNA ("mRNA") polymers which, in turn, serve as templates for formation of structural, regulatory and catalytic proteins from amino acids. Protein synthesis is thus the ultimate form of "expression" of the programmed genetic message provided by the DNA sequence of a gene.

Certain DNA sequences which usually "precede" a gene in a DNA polymer provide a site for initiation of the transcription into mRNA. These are referred to as "promoter" sequences. Other DNA sequences, also usually "upstream" of a gene in a given DNA polymer, bind proteins that determine the frequency (or rate) of transcription initiation. These other sequences are referred to as "regulator" sequences. Thus, sequences which precede a selected gene (or series of genes) in a functional DNA polymer and which operate to determine whether the transcription (and eventual expression) of a gene will take place are collectively referred to as "promoter/regulator" DNA sequences.

The promoter/regulator sequences of genes are clearly susceptible to enormous structural and functional variation and, in fact, only a few such sequences in rather simple genetic systems have been thoroughly structurally and operationally characterized. Promoter/regulator sequences, in general, serve to regulate gene transcription in response to chemical (and sometimes, physical) environmental conditions in and around the cell. Many generalized "models" for the action of promoter/regulator operation in gene transcription and eventual expression in simple, prokaryotic systems have been proposed. One such model posits a "repressor" gene and a regulator sequence or "operator" sequence near the promoter of another gene. According to this model, transcription of the repressor sequence results in expression of a repressor protein which selectively binds to the operator sequence to effectively preclude gene transcription of the selected gene. An environmental "signal" (e.g., increased concentration of a chemical acted upon by the protein product of the gene in question) may operatively inactivate the repressor protein, blocking its ability to bind to the operator sequence in a way which would interrupt transcription of the gene. Increased concentrations of a substrate could be seen as operating to "induce" synthesis of the protein which catalyzes its breakdown.

Another generalized model of operation of promoter/regulator sequences in the regulation of gene transcription posits formation of an initially inactive form of repressor protein by the repressor DNA sequence. Such an inactive form could not bind to an operator DNA sequence (and disrupt selected gene transcription) until it is combined with some other substance present in the cell. The other substance could be, for example, a compound which is the product of a reaction catalyzed by the protein coded for by the selected gene. Increased concentrations of such a reaction product in the cell would thus operate to repress the potential overproduction of proteins responsible for the product's synthesis. In these examples, the regulator protein functions to inhibit transcription. Other regulatory proteins have been described which potentiate or activate transcription of specific DNA sequences. Thus, there are examples of both negative and positive control proteins and corresponding regulatory DNA sequences.

Similar "models" for the operation of promoter/regulator DNA sequences in eukaryotic cells have been proposed. See, e.g., Brown, "Gene Expression in Eukaryotes", Science, 211, pp. 667–674 (1981).

Among the basic problems of genetic engineering is the isolation and preparation of multiple copies of selected gene sequences of interest, together with the promoter/regulator DNA sequences which normally affect their transcription in the cells from which they are isolated. Another basic problem of genetic engineering is the insertion and stable incorporation of DNA sequences into cells in a manner which will permit external regulation of the transcription of the gene sequences and their expression.

Significant advances in the isolation and copying of selected DNA sequences have been made possible by the use of restriction endonuclease enzymes (which are capable of effecting site specific cuts in DNA polymers) and ligating enzymes (which serve to fuse DNA sequences together). DNA sequences of interest are usually incorporated into "vectors" of plasmid or viral origin that allow selective replication in a suitable host cell (for example, bacteria, yeast, or mammalian cells). When these vectors with DNA sequences of interest are introduced into cells of higher animals or plants, they may either be maintained as extrachromosomal elements or incorporated into the chromosomes.

Most genetic engineering activity to date has been directed toward the stable incorporation of exogenous DNA in prokaryotic cells such as bacteria and in the simpler eukaryotes such as yeasts, molds and algae. The hoped-for result of these experiments has been to provide not only a source of multiple copies of selected genes, but the large scale transcription and expression of commercially significant gene in the form of proteinacious products. See, e.g., Cohen, et al., U.S. Pat. No. 4,237,224; Manis, U.S. Pat. No. 4,273,875; and Cohen, U.S. Pat. No. 4,293,652. Work involving eukaryotic cells of higher organisms such as plants and animals has generally involved cells which are capable of continuous growth in culture.

Of significant interest to the background of the invention are numerous publications of prior investigations by the co-inventors and their co-workers relating to: (1) regulation of mammalian gene expression; and (2) introduction of purified genes into eukaryotic cells.

Specifically incorporated by reference herein for purposes of indicating the background of the invention and illustrating the state of the prior art are the following publications of co-inventor Palmiter and his co-workers: Durnam, et al., "Isolation and Characterization of the Mouse Metallothionein-I Gene", P.N.A.S., 77, pp. 6511-6515 (1980); Durnam, et al., "Transcriptional Regulation of the Mouse Metallothionein-I Gene by Heavy Metals", J. Biol. Chem., 256, pp. 5712-5716 (1981); Mayo, et al., "Gluocorticoid Regulation of Metallothionein-I mRNA Synthesis in Cultured Mouse Cells", J. Biol. Chem., 256, pp. 2621-2624 (1981); Hager, et al., "Transcriptional Regulation of Mouse Liver Metallothionein-I Gene by Glucocorticoids", Nature, 291, pp. 340-342 (1981); Glanville, et al., "Structure of Mouse Metallothionein-I Gene and Its mRNA", Nature, 292, pp. 267-269 (1981); and Beach, et al., "Amplification of the Metallothionein-I Gene in Cadmium Resistant Mouse Cells", P.N.A.S., 78, pp. 2210-2214 (1981). The foregoing all deal with the DNA sequence specifying production of a low molecular weight, metal-binding protein found in one or more forms in most vertebrate tissues. More particularly, the publications treat mouse metallothionein genes as well as their promoter/regulator DNA sequences and the responsiveness of the promoter/regulator sequences to metals and steroid hormones.

Additional publications of co-inventor Palmiter and his co-worker which are incorporated by reference herein are: McKnight, et al., "Transferrin Gene Expression, Regulation of mRNA Transcription in Chick Liver by Steroid Hormones and Iron Deficiency", J. Biol. Chem., 255, pp. 148-153 (1980); and Palmiter, et al., "Steroid Hormone Regulation of Ovalbumin and Conalbumin Gene Transcription, A Model Based Upon Multiple Regulatory Sites and Intermediary Proteins", J. Biol. Chem., 256, pp. 7910-7916 (1981).

Also incorporated by reference herein is a publication of co-inventor Brinster and his co-workers dealing with microinjection of plasmids into germinal vesicles of mouse oocytes or pronuclei of fertilized mouse ova, Brinster, et al., "Mouse Oocytes Transcribe Injected Xenopus 5S RNA Gene", Science, 211, pp. 396-398 (1981).

Also pertinent to the background of the present invention and incorporated by reference herein, are the publications of Illmensee, et al., Cell, 23, pp. 9-18 (1981) and Gordon, et al., P.N.A.S., 77, pp. 7380-7384 (1981) which respectively treat injection of nuclei into enucleated mouse eggs and introduction of plasmids containing the herpes thymidine kinase gene and SV40 (Simian virus) sequences into mice. Finally, the recent publication of Wagner, et al. appearing in P.N.A.S., 78 pp. 5016-5020 (1981) and treating incorporation of the human β-globin gene and a functional viral thymidine kinase gene into developing mice, is pertinent to the background of the present invention.

SUMMARY OF THE INVENTION

The present invention provides novel methods and materials for subjecting DNA sequences of living cells and viruses to external regulation with metals and steroid compounds. In one of its aspects, the invention provides for the control of transcription of any selected chromosomal or extrachromosomal gene or DNA sequence through the incorporation of a promoter/regulator DNA sequence which is functionally responsive to environmental variations in the concentration of metals and/or steroid hormone compounds. The invention is thus broadly applicable to numerous procedures for securing control of genetic processes, ranging from the alteration of existing regulation of endogenous genes in prokaryotic and eukaryotic cells to securing selective, differential regulation of expression of selected exogenous genes stably incorporated in "host" cells of eukaryotic organisms including higher animals and plants.

Presently preferred promoter/regulator DNA sequences for use in practice of the invention are derived from avian and mammalian cells and include: the iron and steroid hormone-responsive promoter/regulator sequence naturally associated with the transferrin (conalbumin) gene of chickens; the steroid hormone -responsive promoter/regulator sequence associated with ovalbumin gene in chickens; and the metal and steroid hormone-responsive promoter/regulator sequence of the mouse metallothionein-I or metallothionein II genes.

Novel fusion gene products of the invention include selected DNA sequences to which are ligated metal and/or steroid hormone-responsive promoter/regulator DNA sequences as described above. These products may be incorporated into DNA plasmid and viral vectors to provide useful tools in the transformation of a wide variety of recipient cells.

Processes of the invention include methods for subjecting the transcription of a selected DNA sequence in a living cell or virus to regulation by metals and/or steroids through the site-specific insertion of promoter/regulator DNA sequences responsive thereto. Also comprehended are improvements in prior methods for securing transcription of a selected exogenous DNA sequence in a host cells wherein the DNA sequence is stably incorporated as chromosomal or extrachromosomal constituent of the host. Such improvements comprise fusing to the selected DNA sequence a promoter/regulator DNA sequence capable of selectively promoting or inhibiting transcription of the selected DNA sequence in response to variations in environmental concentration of steroid hormone compounds such as the glucocorticoid, dexamethasone and/or ions of metals such as iron, cobalt, nickel, copper, silver, gold, zinc, cadmium, mercury and bismuth.

Other aspects and advantages of the present invention will be apparent upon consideration of the following detailed description thereof and the drawing wherein FIG. 1 depicts a restriction endonuclease cleavage map for the DNA plasmid pMK which incorporates a fusion gene product of the invention.

DETAILED DESCRIPTION

Figure 1:
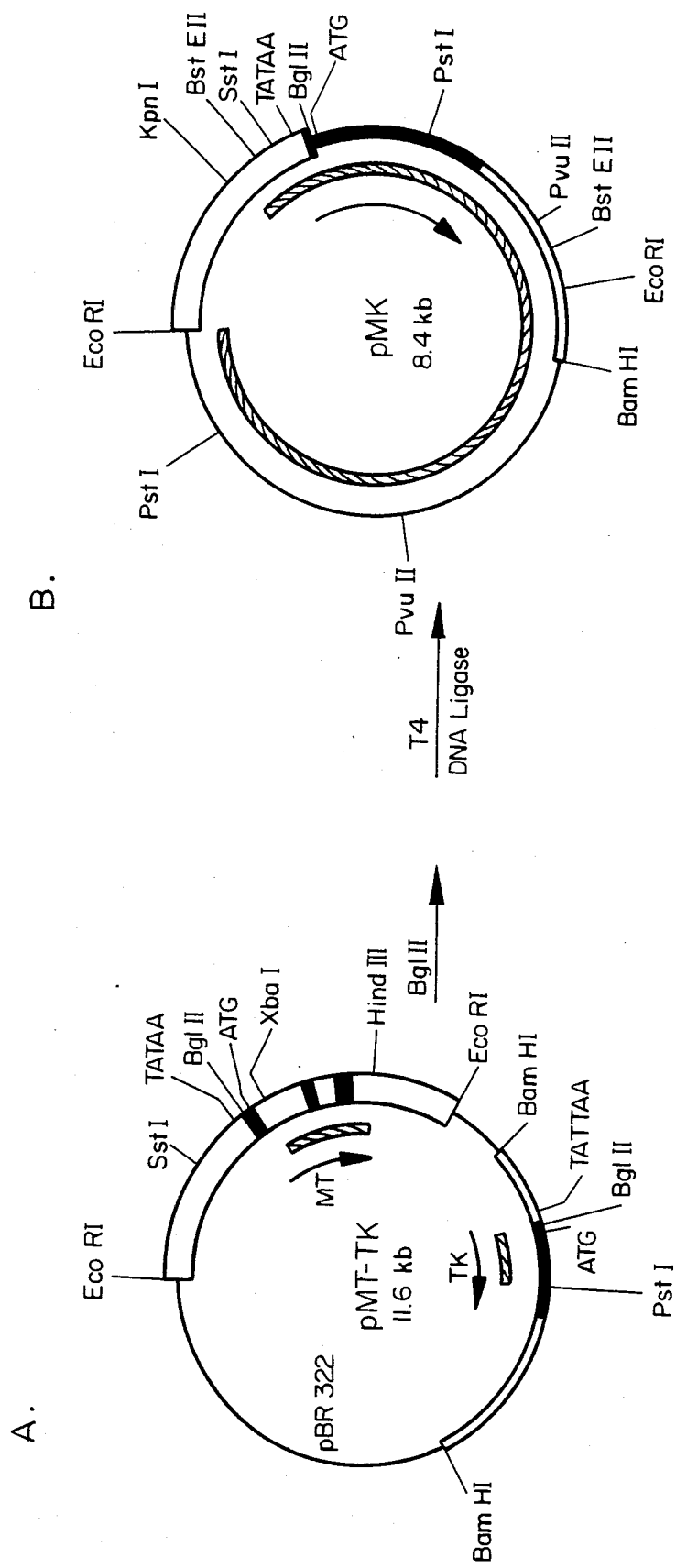

The following illustrative examples are directed to: (a) preparation of a fusion gene as illustrated by plasmid pMK; (b) injection of plasmid pMK into fertilized, one-cell mouse eggs and the manipulation of injected eggs permitting growth of adult mice therefrom; (c) determination of the extent of stable incorporation, transcription and expression of an exogenous gene in the adult mice; (d) mammalian cell culture transformations using the pMK plasmid and effects of metals on exogenous gene expression in the transformed cells; and (e) studies of the transcription and expression of an exogenous gene in mouse embryos injected with the pMK plasmid.

EXAMPLE I

This example relates to procedures for preparation of a fusion gene of the present invention. A DNA plasmid, pMK is shown to include a DNA sequence coding for herpes simplex virus (HSV) thymidine kinase (TK) which is operatively associated with the promoter/regulator DNA sequence of the mouse metallothionein-I (MT-I) gene.

Durnam, et al., *P.N.A.S.*, 77, pp. 6511–6515 (1980) discloses the construction of DNA plasmid $m_1pEE_{3.8}$ which comprises bacterial plasmid pBR322 containing a 3.8 kilobase genomic Eco RI fragment, which includes the mouse MT-I gene, inserted into the Eco RI site of the plasmid. The MT-I gene spans about 1.1 kb pairs and contains at least two introns.

As shown in FIG. 1, part A, plasmid pMT-TK was constructed from plasmid $m_1pEE_{3.8}$ by insertion of the 3.5 kb Bam HI fragment of Herpes Simplex Virus Type I containing the thymidine kinase gene [See, McKnight, *Nuc. Acid. Res.*, 8, pp. 5949–5964 (1980)] into the Bam HI site. The two genes are present in the same transcriptional orientation, as shown by the arrows. As illustrated in FIG. 1, part B, the fusion plasmid pMK, was created by digestion of plasmid pMKT-TK with Bgl II restriction endonuclease followed by ligation with T4 DNA Ligase to directly join the 5′ region of the MT-I gene, (the promoter/regulator sequence of MT-I), to the TK structural gene. pBR322 sequences are shown by a single line, TK gene sequences by a narrow box, and MT-I gene sequences by a wide box. mRNA coding regions are represented by closed boxes; non-transcribed and intron regions are shown by open boxes. Hatched boxes inside the circles represent regions of these genes that were used as hybridization probes; the MT-I specific probe, "MT-XH" extends from Xba I to Hind III and TK-specific probe "TK-BP" extends from Bgl II to Pst I. The fusion plasmid probe "pMK(-EK)" includes the entire plasmid except the Eco RI to Kpn I region because Southern blots revealed that this is a sequence present many times in the mouse genome. Restriction sites relevant to the construction of the plasmids and the gene-specific probes are shown in FIG. 1, part A. All restriction sites used in mapping integrated copies of pMK are shown in FIG. 1, part B. pMK is not cut by Hind III, Xba I, or Xho I. Also shown are the locations of the TATAA "promoter" sequences and ATG translation start codons for the two genes.

EXAMPLE II

This example relates to the use of the fusion gene-carrying plasmid, pMK, as a vector for microinjection into the pronuclei of fertilized mouse ova and to growth of the ova into adult mice which have pMK DNA sequences incorporated into somatic and germ cells.

pMK DNA according to Example I was isolated from a cleared lysate of bacterial cells by SDS-proteinase K treatment followed by phenol:chloroform extraction and ethanol precipitation. The nucleic acids were digested with RNase A and passed through Bio-Gel A50m column in 0.1X SET (1X SET=1% SDS, 5 mM EDTA, 10 mM Tris, pH 7.5) to separate DNA from RNA fragments. The preparation used for these experiments contained about ⅓ supercoiled plasmids, ⅓ nicked circles, and about ⅓ larger oligomers of the plasmid, as revealed by agarose gel electrophoresis and ethidium bromide staining.

Fertilized one-cell ova of C57×SJL hybrids were flushed from the oviduct using Brinster's medium [see, Brinster, pp. 251–286 in "Growth, Nutrition and Metabolism of Cells in Culture", Vol. 2, Rothblat and Cristofala, eds., N.Y., Academic Press (1972)] on the morning of day one of pregnancy. Cumulus cells were removed from ova with hyaluronidase (300 U/ml) and the ova were washed free of debris and enzyme before manipulation. For injection, the ova were transferred to a depression slide in Brinster's medium containing 5 μg/ml cytochalasin B and were held in place by a blunt pipette while the tip of the injector pipette was inserted through the zona pellucida and vitellus and into the male pronucleus [Brinster, et al., *Science*, 211, pp. 396–398 (1981)]. The DNA solution in the injector pipette was slowly discharged into the nucleus using a syringe connected to a micrometer. The larger pronucleus (male) of the fertilized ovum was injected with approximately 2 pl of plasmid solution containing a total of about 200 copies of the pMK plasmid. Following injection, the ova were washed free of cytochalasin and returned to the same medium used for collection. When injections were completed, the ova were transferred to the oviducts of pseudopregnant, random-bred Swiss mice.

An average of 16 eggs were then transferred into the oviducts of 15 pseudopregnant mice. Six of these mice had litters providing a total of 12 male and 7 female offspring. At the age of 4 weeks, each of the males was mated with a normal female. Before assaying for gene expression, the mice were injected with $CdSo_4$ (2 mg/kg). This was done in the hope of inducing HSV TK activity since this dose was shown to induce MT-I mRNA in liver and kidney [Durnam, et al., *P.N.A.S.*, 77, pp. 6511–6515 (1980)]. Eighteen hours later the mice were killed, liver samples were prepared for TK assay and the remainder of each animal was frozen for subsequent nucleic acid analysis.

EXAMPLE III

This example relates to assays performed on tissue of adult mice of the previous example.

For initial TK assay, 5 μl of a 20% liver homogenate was tested. One animal (#23-2) showed about 40-fold more activity than the others. However, this activity was so high that it was in the non-linear range of the assay. After appropriate dilution about 200-fold more TK activity was measured in this mouse compared to litter mates and other mice of similar age. To ascertain whether the TK activity was derived from the HSV TK gene or from the endogenous mouse gene, an antibody specific for HSV TK was mixed with the liver extracts prior to enzyme assay. The TK activity of mouse 23-2 was inhibited 97% with this antisera, whereas the TK activity of the other mice was essentially unaffected.

Additional assays confirmed that the majority of TK activity of mouse 23-2 was due to the HSV gene product. The endogenous mouse TK enzyme cannot phosphorylate iododeoxycytidine (IdC) whereas the HSV enzyme can. Thus, IdC will inhibit the conversion of [$^3$H]thymidine to [$^3$H]thymidylic acid if the enzyme is of viral origin. This was observed with the enyzme preparation from mouse 23-2, but not from the litter mates. The substrate specificity of the mouse and HSV TK enzymes can also be demonstrated using $^{125}$IdC and tetrahydrouridine, an inhibiter of cytidine deaminase. In crude liver extracts from normal mice, $^{125}$IdC is converted into phosphorylated derivatives due to the action of deaminases that convert $^{125}$IdC to iododeoxyuridine which can be phosphorylated by TK. However, when an inhibitor of deaminase (tetrahydrouridine, THU) is included in the assay, labeled substrates for the endogenous TK enzyme are not formed and the apparent activity is inhibited 30-fold. In contrast, the TK activity in mouse 23-2 is inhibited only 20% as would be expected with a viral enzyme that can utilize $^{125}$IdC directly.

To assay for the presence of the MK fusion gene in the mice, kidney DNA was digested with restriction enzyme, Bst EII, electrophoresed on an agarose slab gel and blotted according to the method of Southern [J. Mol. Biol., 98, pp. 503–517 (1975)]. Nick translated probes were used that would detect both the endogenous MT-I gene and any fusion gene. The endogenous MT-I gene falls within a 6 kb Bst EII fragment, whereas the MK fusion gene would be cut into a 2.3 kb fragment by this enzyme (see FIG. 1, part B). DNA from mouse 23-2 and three additional mice (#19-2, #21-3 and #23-1) were found to have the 2.3 kb band expected of the MK gene. The MK gene band had approximately half the intensity, as measured by densitonmetry, as the MT-I gene band in all of the mice except 19-2, in which the MK band is about 6 times more intense. To estimate the number of MK genes per cell, a control experiment was performed in which the same combination of probes was hybridized to equal molar amounts of the MT-I and MK genes. This was done by digesting pMT-TK (FIG. 1, part A) with Eco RI or Pvu II and separating the MT-I gene and MK gene containing fragments by agarose gel electrophoresis. Different amounts of the digests (40 to 160 pg of plasmid DNA) were electrophoresed to facilitate quantitation. The autoradiographic band representing the MT-I gene was consistently 4 fold more intense than the band representing the MK gene. Since in previous experiments the MT-I gene band was only twice as intense as the MK gene band, it can be concluded that there must be twice as many MK genes per cell as MT-I genes. Thus, knowing that there are 2 MT-I genes per cell, it can be inferred that there are 4 MK genes per cell in these mice. By the same calculation, it was estimated that mouse 19-2 has about 48 copies of the MK gene per cell.

Since HSV TK enzyme activity was not detected in mice 19-2, 21-3 or 23-1 even though intact MK genes were present, a check as to whether the mice were actually induced with Cd was made by measuring the amount of MT-I mRNA by solution hybridization with $^{32}$P-labeled MT-I cDNA. All of the mice had between 600 and 2700 molecules of MT-I mRNA per liver cell. The basal level of MT-I mRNA in mouse liver was variable but averaged about 150 molecules per cell, whereas after optimal induction levels of about 2300 molecules per cell are generally obtained (Durnam, et al., supra). This control indicates that at the time the mice were killed the MT-I gene was still induced and suggests that the lack of thymidine kinase activity was not due to the failure of Cd delivery to the tissues.

HSV TK mRNA levels were also measured by solution hybridization with a $^{32}$P-labeled HSV TK cDNA. Although TK mRNA was detectable in the liver of mouse 23-2, the level was only 28 molecules per cell. A low amount of HSV TK mRNA was also detected in mouse 19-2, the mouse with nearly 50 copies of the MK gene. All other mice had less than 2 molecules of TK mRNA per cell.

The MK gene was found to be present in several different tissues of mouse 23-2, including liver, kidney, brain, muscle and testis, and the intensity of the hybridizing band was similar in each tissue suggesting that the gene copy number is constant in each tissue. HSV·TK activity and mRNA levels were lower in kidney than in liver and were undetectable in brain. Thus, MK gene expression closely paralleled the MT-I gene expression in those tissues.

To ascertain whether the pMK plasmid was integrated into the mouse genome, DNA from each of the 4 mice that were positive for the MK gene was digested with several enzymes that cut twice, once, or not at all within the pMK plasmid. After electrophoresis and blotting, the nitrocellulose was hybridized with a nick-translated probe that includes all of the plasmid except the 1150 bp between Eco RI and Kpn I; this region was omitted because it contains a repeat sequence. Predictions of what size bands would be produced are quite different depending on whether the pMK plasmid is integrated into the mouse genome or not. For example, with enzymes that cut once within a single integrated plasmid would be expected to generate only junction fragments, i.e., fragments that combine both plasmid and genomic sequences, and they would be of different size than predicted from the plasmid.

Restriction of liver DNA from each of the mice that were positive for MK genes with enzymes, Bam Hl, Bgl II, or Kpn I, that cut only once within pMK revealed a prominent 8.4 kb fragment that was the same size as that predicted from an unintegrated plasmid. Likewise, enzymes that cut twice within pMK such as Bst EII, Eco RI and Pvu II, give two prominent bands that add up to 8.4 kb, the size of pMK. However, when enzymes were used that do not cut within pMK, such as Hind III and Xba I, the hybridizing DNA was nearly as large as uncut genomic DNA; no bands corresponding to unintegrated single plasmids were observed. A possible resolution of this paradox is that several copies of pMK are tandemly duplicated in times and integrated at a single site. Restriction of DNA with this configuration would generate fragments corresponding to the original plasmid plus two junction fragments that would be less than 1/n th as intense. Indeed, in addition to the intense bands there are typically several additional fainter bands. One of these faint bands corresponded to the MT-I gene, which would be expected because about 650 bp of the probe are homolgous to sequences 5' of the MT-I gene. The other faint bands were good candidates for the predicted junction fragments. The average intensity of the junction fragments from mouse 23-2 relative to the main band(s) is about 1/5 th, suggesting that the intact pMK plasmid was repeated about 5 times in this mouse.

To test this idea of tandem duplication, high molecular weight DNA from mouse 23-2 was isolated and cut with a battery of enzymes that do not cut within plasmid pMK in an effort to cut the pMK repeat unit to a minimal size. It was found that the size of the hybridizing band was greater than 45 kb (the largest marker) in uncut DNA and between 23 and 45 kb after restriction with Hind III, Xba I and Xho I, whereas total mouse DNA was cut to a weight average size of about 2 kb as shown by ethidium bromide straining. When Bam Hl was added along with the other enzymes the 8.4 kb Bam Hl linear fragment was obtained along with several fainter fragments that probably represented the predicted junction fragments. Thus, it was concluded that there were 4 or 5 direct repeats of the pMK plasmid in mouse 23-2, a result that is consistent with the relative intensity of the 8.4 kb band and the junction fragments as well as gene dosage.

The efficiency of achieving plasmid integration and expression in the above experiment is remarkably good. Nineteen offspring (12 males and 7 females) of the first experiment were assayed for TK expression and one, 23-2, was clearly positive. The DNA from the 12 males was assayed and four were positive. In a second experiment, the pMK plasmid was augmented by inserting the Bam Hl fragment from the vector of Mulligan, et al., Nature, 227, pp. 108-114 (1980), pSV3-gpt, which contains the SV40 origin and T-antigen gene. Twelve offspring were analyzed for TK expression and pMK DNA and all were negative. In a third experiment, the original plasmid was linearized and ligated to mouse DNA prior to injection. In this experiment, 5 offspring have now been analyzed and 2 express HSV TK and have the MK gene. In a fourth experiment, a linear 2.3 kb Bst E2 fragment that includes the MK gene was injected and 1 out of 5 mice are positive for HSV TK expression. The number of offspring is too low for good statistics and hence it is not known whether the variations in protocol are significant, but overall 4 mice have been obtained that express HSV TK and an additional 3 that have intact MK genes but do not express TK out of 41 offspring that have been analyzed.

EXAMPLE IV

This example relates to transfection of mammalian cells in culture with a fusion gene product of the invention incorporated into a plasmid vector. More specifically, the example illustrates transfection of mouse $L_{TK^-}$ cells with pMK plasmids.

All cells were grown in Ham's F12 with 10% newborn calf serum (Grand Island Biological Co.), $L_{TK^-}$ cells were obtained from G. Merrill, (University of Washington). The methods for transfection have been described by Wigler, et al., Cell, 14, pp. 725-731 (1978). Briefly, 2 μg of the appropriate vector DNA was mixed with 18 μg of carrier herring sperm DNA in 375 μl TE (L mM Tris, pH 7.9, 01. mM EDTA), 125 μl 1M $CaCl_2$ was added, and the entire mixture was added slowly and with agitation to 500 μl of 2X Hepes-buffered saline (280 mM NaCl, 50 mM Hepes, 1.5 mM $Na_2PHO_4$, pH 7.1. The precipitate was allowed to form for 30 min at room temperature and as added to a 100 mm dish of cells in 10 ml of medium. Cells were plated at $8 \times 10^5$ per dish one day prior to transfection, and were fed fresh medium 4 hr prior to transfection. One day after transfection, cells were placed in selective HAT medium (15 μg/ml) hypoxanthine, 0.2 μg/ml aminopterin, 5 μg/ml thymidine) with or without 10 μM Cd. Selective medium was changed every 3 days. When Cd was used in the selection, it was removed 2 weeks prior to harvesting the cells. Individual colonies were cloned using glass cylinders and expanded in selective medium.

Transfection of mouse $L_{TK^-}$-cells with pMK resulted in clones wherein thymidine kinase activity was inducible by cadmium, but not dexamethasone.

EXAMPLE V

The present example illustrates the study of transcriptional regulation of HSV thymidine kinase activity in mouse ova injected with plasmid pMK.

Microinjection procedures were carried out as in Example 2. The $^3$H-thymidine kinase assays were performed in the following manner. After injection of the plasmid, the ova were divided randomly into two groups and were incubated 22 hr in Brinster's medium and then transferred to 200 μl of hypotonic buffer (10 mM KCl, 2 mM $MgCl_2$, 10 mM tris HCl, pH 7.4, 1 mM atp, 10 mM β-mercaptoethanol, 50 mM ε-aminocaproic acid and 1 mg ml$^{-1}$ bovine serum albumin)[21]. One group included 50 μM cadmium in the medium and the other did not. The cells were frozen and thawed three times and 20 μl of reaction mixture (150 mM Tris HCl, pH 7.5, 10 mM ATP, 10 mM $MgCl_2$, 25 mM NaF, 10 mM β-mercaptoethanol) was added followed by 5 μl of water containing 5 μCi $^3$H-thymidine (80 Ci mmol$^{-1}$; New England Nuclear). The mixture was incubated for 2 hr at 37°, and the $^3$H-TMP produced was measured by adsorbtion on to DE-81 and subsequent scintillation counting.

Table 1 below sets out the results of analysis of thymidine kinase activity with varying numbers of plasmids injected, with and without cadmium induction. Values for $^3$H-TMP formed are the mean of 25 ova in two separate experiments.

TABLE 1

Regulation Of Thymidine Kinase Activity Produced From The Fused pMK Gene By Cadmium

| Number of pMK plasmids injected | Formation of $^3$H—TMP (cpm × $10^{-3}$)[b] | |
|---|---|---|
| | Ova cultured without Cd | Ova cultured in 50 μM Cd |
| 2,000 | 190.0 | 2,364.3 |
| 200 | 25.3 | 268.4 |
| 20 | 8.3 | 12.2 |
| 0 | 8.5 | 8.8 |

No increase in TK activity in response to dexamethasone treatment could be determined, possibly due to the lack of glucocorticoid receptors in the cells.

Studies of thymidine kinase activity in ova treated with restriction fragments derived from pMK reveal significant cadmium regulation for fragments resulting from restriction with Bgl II, (with and without blunt-ending of fragments with DNA Polymerase I). Similar, but significantly less profound results were obtained where the HSV TK structural gene and the MT-I promoter/regulator sequence were separately injected or were religated in vitro and jointly injected as a single DNA linear fragment.

While the above examples illustrate practice of the invention in the general context of responsiveness of the mouse metallothionein-I gene promoter/regulator DNA sequence to cadmium, it will be apparent that there are numerous other substances to which that particular sequence is sensitive and which therefore may be used to control fused gene expression. Other metals useful in practice of the invention include iron, cobalt, nickel, copper, silver, gold, zinc, mercury and bismuth. Based on studies of the MT-I promoter/regulator sequence in mice, steroids to which the sequence may be responsive include estrogens, progestins, androgens and, especially, glucocorticoids such as dexamethasone. The lack of demonstrable dexamethasone responsiveness of the MT-I promoter/regulator sequence in the above transformations involving plasmid pMK may indicate that a somewhat larger 5' MT-I sequence (than present in pMK) is needed to retain steroid responsiveness or merely that some modifications in the experimental manipulation are necessary.

As previously noted, other metal and/or steroid hormone-responsive promoter/regulator sequences suitable for use in practice of the invention are contemplated. Preferably, these would include those of mammalian and avian cell origin (such as the sequences associated with transcription and expression of chicken ovalbumin and transferrin (conalbumin) genes, and the mouse metallothionein-II gene), as well as viral sequences (e.g., mouse mammary tumor virus). These promoter/regulator sequences may be responsive to a variety of steroids including estrogens, projestins, and androgens as well as glucocorticoids.

While plasmid vectors, as exemplified by pMK are suitable for many embryo injection and transformation procedures according to the invention, it will be understood that many other vectors can be constructed to carry a DNA sequence of choice to which is fused a metal and/or steroid hormone-responsive promoter/regulator DNA sequence.

The formation of fusion genes for use in stably incorporating exogenous DNA sequences into host cells is specifically illustrated in above examples. It is within the contemplation of the invention that eukaryotic and viral genomes can be made the subject of a site-specific insertion of an endogenous or exogenous metal and/or steroid hormone-responsive promoter/regulator DNA sequence by means of the procedures set out in, e.g., Mocarski, et al., *Cell,* 22, pp. 243–245 (1980); Post, et al., *Cell,* 24, pp. 555–565 (1981); and Post, et al., *Cell,* 25, pp. 227–232 (1981).

Numerous modifications and variations of the invention as described and illustratively exemplified above are expected to occur to those skilled in the art. As one example, the invention is expected to be most useful in securing control of transcription of DNA sequences in higher animals (such as cattle), and plants so as to correct genetic defects provide resistance to disease or promote favorable genetic characteristics. Consequently, only such limitations as are set out in the claims should be placed thereon.

What is claimed is:

1. A process for subjecting the transcription of a selected DNA sequence to external control under given environmental conditions which comprises the steps of:
   providing a selected isolated structural gene that is transcriptionally responsive to a mouse metallothionein-I promoter/regulator DNA sequence under the given environmental conditions; and
   operatively fusing the selected structural gene with said promoter/regulator DNA sequence.

2. In the genetic engineering process for securing transcription and expression of a selected isolated structural gene sequence in a mammalian host cell wherein said selected structural gene is stably incorporated as a chromosomal or extrachromosomal constituent of the host, the improvement comprising the step of:
   operatively fusing with said selected structural gene sequence a mouse metallothionein-I promoter/regulator DNA sequence which is responsive to environmental variations within the host cell in the concentration of ions of metal.

3. A fusion gene product, suitable for use in genetic transformation of a mammalian host cell, said product comprising: a non mouse metallothionein structural gene sequence to be incorporated in said host cell operatively fused with a mouse metallothionein-I promoter/regulator DNA sequence.

4. A genetic transformation vector comprising a DNA plasmid or virus including a fusion gene according to claim 3.

* * * * *